(12) United States Patent
Ritchie et al.

(10) Patent No.: US 11,992,548 B2
(45) Date of Patent: May 28, 2024

(54) HAIR TREATMENT COMPOSITIONS, KITS, AND METHODS OF USE

(71) Applicant: L'OREAL, Paris (FR)

(72) Inventors: Erika Suzanne Ritchie, South Plainfield, NJ (US); Rachel Ferebee Maher, Morristown, NJ (US); Ronak Rughani, Edison, NJ (US)

(73) Assignee: L'OREAL, Paris (FR)

( * ) Notice: Subject to any disclaimer, the term of this patent is extended or adjusted under 35 U.S.C. 154(b) by 106 days.

(21) Appl. No.: 17/104,240

(22) Filed: Nov. 25, 2020

(65) Prior Publication Data
US 2021/0154125 A1    May 27, 2021

Related U.S. Application Data

(60) Provisional application No. 62/941,394, filed on Nov. 27, 2019.

(51) Int. Cl.
| | | |
|---|---|---|
| *A61K 8/73* | (2006.01) | |
| *A61K 8/22* | (2006.01) | |
| *A61K 8/67* | (2006.01) | |
| *A61Q 5/00* | (2006.01) | |
| *A61Q 5/12* | (2006.01) | |

(52) U.S. Cl.
CPC .............. *A61K 8/73* (2013.01); *A61K 8/22* (2013.01); *A61K 8/676* (2013.01); *A61Q 5/002* (2013.01); *A61Q 5/12* (2013.01)

(58) Field of Classification Search
None
See application file for complete search history.

(56) References Cited

U.S. PATENT DOCUMENTS

| | | | | |
|---|---|---|---|---|
| 4,530,829 | A * | 7/1985 | Abe | A61Q 5/00 424/DIG. 2 |
| 5,981,718 | A | 11/1999 | Olsen et al. | |
| 6,201,110 | B1 | 3/2001 | Olsen et al. | |
| 6,264,929 | B1 * | 7/2001 | Karlen | A61K 8/361 424/70.22 |
| 6,416,756 | B1 | 7/2002 | Olsen et al. | |
| 6,425,403 | B1 | 7/2002 | Lin Lu et al. | |
| 6,495,136 | B1 | 12/2002 | Weisgerber et al. | |
| 6,685,952 | B1 | 2/2004 | Ma et al. | |
| 2005/0036970 | A1 * | 2/2005 | Sabbagh | A61K 8/44 424/70.2 |
| 2011/0067722 | A1 * | 3/2011 | Bureiko | A61Q 5/10 8/406 |
| 2013/0319449 | A1 | 12/2013 | Xavier et al. | |
| 2016/0220471 | A1 | 8/2016 | Baghdadli et al. | |
| 2017/0360679 | A1 * | 12/2017 | Savaides | A61K 8/36 |
| 2019/0328637 | A1 | 10/2019 | Parikh et al. | |
| 2020/0281839 | A1 | 9/2020 | Philippe et al. | |

FOREIGN PATENT DOCUMENTS

| | | | | |
|---|---|---|---|---|
| CN | 105496807 A | 4/2016 | | |
| JP | 2011102244 A | 5/2011 | | |
| WO | WO-0006094 A1 * | 2/2000 | | A61K 8/23 |
| WO | 2013076061 A2 | 5/2013 | | |
| WO | WO-2013069167 A1 * | 5/2013 | | A61K 8/046 |
| WO | 2015018853 A1 | 2/2015 | | |
| WO | 2016142551 A1 | 9/2016 | | |

OTHER PUBLICATIONS

International Search Report and Written Opinion issued on Mar. 9, 2021 for corresponding PCT Application No. PCT/US2020/062174.
Database GNPD; Mintel; "Hair Colourant," 2014 XP055778733.

* cited by examiner

*Primary Examiner* — Tigabu Kassa
(74) *Attorney, Agent, or Firm* — POLSINELLI PC

(57) ABSTRACT

Hair treatment compositions, kits for producing such hair treatment compositions, and methods for using such kits and/or hair treatment compositions are provided for treating hair. Methods for treating hair typically include: obtaining a first composition comprising one or more polysaccharides with amine group(s) and water; adding ascorbic acid and one or more peroxides, peroxo compounds, or combinations thereof to the first composition to obtain a second composition; applying the second composition to hair; and heating the hair, which has the second composition applied thereto, to a temperature above 25° C. Kits for improving hair typically include a first composition comprising one or more polysaccharides with amine group(s) and water; a second composition comprising up to 100 wt. % of ascorbic acid; and a third composition comprising a peroxide, a peroxo compound, or a combination thereof, wherein the first composition, the second composition, and the third composition are separately contained.

18 Claims, No Drawings

HAIR TREATMENT COMPOSITIONS, KITS, AND METHODS OF USE

CROSS-REFERENCE TO RELATED APPLICATIONS

This application claims the benefit of U.S. Provisional Patent Application No. 62/941,394, filed Nov. 27, 2019, which is incorporated by reference herein in its entirety.

FIELD OF THE DISCLOSURE

The present disclosure relates to hair treatment compositions, kits for producing such hair treatment compositions, and methods for using such kits and/or hair treatment compositions.

BACKGROUND OF THE DISCLOSURE

Many hair styling and beautifying treatments have been developed to change the appearance of hair, including many chemical treatments. Chemical treatments include, for example, hair bleaching and coloring, permanents, waving products, and relaxing treatments (straightening treatments). While these chemical treatments may provide an improved style and/or color to the hair, these treatments often cause a certain degree of damage to the hair. Environmental factors, such as salt water, sunlight, and heat, can also damage hair.

Damaged hair is characterized by unnatural changes to the protein structure of the individual hair strands or shafts. The damage to hair can produce split ends, dry straw-like hair, hair that is easily broken, and hair that is "frizzy" and unmanageable. Because the visible portion of hair is dead, it has no ability to regenerate itself.

There are numerous over-the-counter and salon treatments that purport to repair damaged hair. These include conditioners, hot oil treatments, hydrolyzed proteins, vitamin formulations, and exotic fruit, leaf, or root extracts. These treatments, however, provide only limited improvement to the hair. Therefore, hair repair technologies that restore the properties of hair back to their natural level are desired.

SUMMARY OF THE DISCLOSURE

Aspects of the disclosure are directed to hair treatment compositions, kits for producing such hair treatment compositions, and methods for using such kits and/or hair treatment compositions. The hair treatment compositions, kits, and methods disclosed herein are directed to providing improved hair attributes, such as strengthening of the hair fiber, protecting hair fibers from damage or further damage, and/or improving cosmetic attributes of the hair, including smoothness, alignment of the hair, closure of the hair ends, shine, conditioning, and appearance.

In accordance with one aspect of the disclosure, a hair treatment composition is provided for treating hair. The hair treatment compositions are typically formulated to form a film on the hair. In some instances, the hair treatment compositions form a film that is grafted onto the hair, e.g., by bonding to the proteins of the hair. Without being limited to any particular theory, the inventors speculate that hair treatment compositions may form a film that forms an amide bond between the amines from the chitosan with the carboxylic acids from the hair proteins (such as aspartic acid or glutamic acid) to and/or ester bonds are formed between the hydroxyl group on the chitosan and the carboxylic acids from the hair proteins to create ester bonds. The hair treatment composition may be formulated to provide enhanced benefits, such as those discussed above, when heated to a temperature of above 25° C. by applying heat, e.g., at a temperature of about 30° C. to about 80° C.

The hair treatment compositions typically contain at least:
a) one or more polysaccharides with amine group(s);
b) ascorbic acid;
c) one or more peroxides, peroxo compounds, or combinations thereof; and
d) water.

The one or more polysaccharides with an amine group(s) may be selected from polyhexosamines, organic or mineral acid salts thereof, α or β anomers thereof, isomers thereof of L or D configuration, and solvates/hydrates. Preferably, the one or more polysaccharide with an amine group(s) comprises or consists of chitosan. In some instances, the one or more polysaccharide with amine group(s) may, optionally, be solubilized in water.

Additionally, the hair treatment composition may include one or more acids other than ascorbic acid, such as those chosen from non-polymeric acids having a structure that is linear, aromatic, or phenolic. For example, the one or more acids other than ascorbic acid may be chosen from carboxylic acids, fatty acids, and mixtures thereof. In at least one instance, the one or more acids other than ascorbic acid are chosen from tannic acid, caffeic acid, acetic acid, citric acid, gallic acid, and mixtures thereof.

The one or more peroxides, peroxo compounds, or combinations thereof may comprise or consist of hydrogen peroxide. Additionally or alternatively, the hair treatment composition may have a pH of about 2 to about 6, such as e.g., about 3 to about 4. In at least one instance, the hair treatment composition is not an emulsion.

According to another aspect of the disclosure, a kit is provided for treating hair. The kits may be used by hair-care professionals and salons for treating the hair of patrons or the kits may be purchased and used at home directly by consumers. The kits may include or more compounds discussed with reference to the hair treatment composition. The kits disclosed herein typically include:
(1) a first composition comprising one or more polysaccharides with amine group(s) and water;
(2) a second composition comprising up to 100 wt. % of ascorbic acid based on the total weight of the second composition; and
(3) a third composition comprising a peroxide, a peroxo compound, or a combination thereof,
wherein the first composition, the second composition, and the third composition are separately contained.

In accordance with a further aspect of the disclosure, methods are provided for using the hair treatment compositions and/or kits disclosed herein. Methods for treating hair typically include:
i) obtaining a first composition comprising one or more polysaccharides with amine group(s) and water;
ii) adding ascorbic acid and one more peroxides, peroxo compounds, or combinations thereof to the first composition to obtain a second composition;
iii) applying the second composition to hair; and
iv) optionally, heating the hair, which has the second composition applied thereto, to a temperature above 25° C.

The hair may, in some instances, be heated at a temperature of about 30° C. to about 80° C., e.g., using a hair blow dryer. The method may also include heating the hair for a period of about 1 minute to about 1 hour. Additionally, the method may include or use one or more compounds and/or compositions discussed herein with reference to the hair treatment composition and/or the kits. The methods may also improve the color retention of artificially colored hair. For example, the method may include applying the second composition to hair that has been artificially colored hair with at least one die, pigment, or a combination thereof, preferably within 1 hour of artificially coloring such hair, to improve the color retention of the artificially colored hair.

DETAILED DESCRIPTION OF THE DISCLOSURE

Aspects of the disclosure are directed to hair treatment compositions, kits for producing such hair treatment compositions, and methods for using such kits and/or hair treatment compositions. The hair treatment compounds, kits, and methods disclosed herein advantageously provide improved hair attributes, such as strengthening of the hair fiber, protecting hair fibers from damage or further damage, and/or improving cosmetic attributes of the hair, including smoothness, alignment of the hair, closure of the hair ends, shine, conditioning, and appearance.

The hair treatment compositions typically contain at least:
a) one or more polysaccharides with amine group(s);
b) ascorbic acid;
c) one or more peroxides, peroxo compounds, or combinations thereof; and
d) water.

The hair treatment composition may include one or more acids other than ascorbic acid, such as those chosen from non-polymeric acids having a structure that is linear, aromatic, or phenolic. It is believed that adding one or more acids other than ascorbic acid, such as those disclosed herein, may improve certain desirable attributes provided by the hair treatment compositions and/or kits. In some instances, the one or more acids other than ascorbic acid may be chosen from carboxylic acids, fatty acids, and mixtures thereof. In at least one instance, the one or more acids other than ascorbic acid are chosen from tannic acid, caffeic acid, acetic acid, citric acid, gallic acid, and mixtures thereof. Additionally, the hair treatment composition may have a pH of about 2 to about 6, such as e.g., about 2.5 to about 5, about 3 to about 4, or about 3.2 to about 3.7.

The benefits provided by the hair treatment compositions or kits disclosed herein may be enhanced by the method for using such hair treatment compositions or kits. For example, the method may include heating the hair to above 25° C. by applying heat at a temperature of about 30° C. to about 80° C. after the hair has been applied with the hair treatment composition. Without being limited to any particular theory, the inventors believe that heating the hair to certain temperatures with a blow dryer set to specific temperature ranges may improve attributes provided by a film formed from the hair treatment compositions comprising polysaccharide(s) with amine group(s), ascorbic acid, and a peroxide(s), peroxo compound(s), or combination(s) thereof.

Suitable components, such as those listed below, may be included or excluded from the formulations for the skin-tightening compositions depending on the specific combination of other components, the form of the skin-tightening compositions, and/or the use of the formulation.

Polysaccharides with Amine Group(s)

The hair treatment compositions include one or more polysaccharides with amine group(s) typically in an amount of about 0.1 to about 10 wt. %, based on the total weight of the hair treatment composition. For example, the total amount of polysaccharides with amine group(s) may be about 0.1 to about 10 wt. %, about 0.1 to about 8 wt. %, about 0.1 to about 5 wt. %, about 0.1 to about 3 wt. %; about 0.5 to about 10 wt. %, about 0.5 to about 8 wt. %, about 0.5 to about 5 wt. %, about 0.5 to about 3 wt. %; from about 0.8 to about 10 wt. %, about 0.8 to about 8 wt. %, about 0.8 to about 5 wt. %, about 0.8 to about 3 wt. %; or about 0.8 to about 2 wt. %, including all sub-ranges therebetween, based on the total weight of the hair treatment composition.

The polysaccharides with amine group(s) may include organic or mineral acid salts thereof, the α or β anomers thereof, the optical isomers thereof of L or D configuration, and the solvates thereof such as hydrates. In some cases, the polysaccharide(s) with amine group(s) have an average molecular weight MW of less than or equal to 400 kDa, e.g. less than 200 kDa. Similarly, in some cases, the polysaccharide(s) with amine group(s) have a low average molecular weight MW, i.e. a MW<100 kDa, preferentially having an average MW which is <40 kDa, more preferentially having an average MW that is between 1 kDa and 30 kDa inclusive, more preferentially having an average MW that is between 3 kDa and 28 kDa inclusive.

The polysaccharide(s) with amine group(s) may be natural, of animal or plant origin, or derived from synthesis, hemisynthesis or biosynthesis. According to at least one particular embodiment, the polysaccharide(s) with amine group(s) are chosen from those with $C_5$-$C_7$ saccharide units and also the organic or mineral acid salts thereof, the α or β anomers thereof, the optical isomers thereof of L or D configuration, and the solvates thereof such as hydrates.

More particularly, the polysaccharide(s) with amine group(s) may be a $C_6$ saccharide unit with amine group(s). These polysaccharides with amine group(s) are generally referred to as polyhexosamines. According to at least one particular embodiment, the saccharide units of the polysaccharide with amine group(s) are of β (beta) anomeric configuration and/or D configuration.

In some cases, the saccharide units of the polysaccharide with amine group(s) are joined to one another between the C1 carbon atoms of one saccharide unit and the C4 carbon atoms of the other saccharide unit, denoted (1→4), such as the polysaccharide with amine group(s) of formula (B) below, and also the organic or mineral acid salts thereof, the α or β anomers thereof, the optical isomers thereof of L or D configuration, and the solvates thereof such as hydrates:

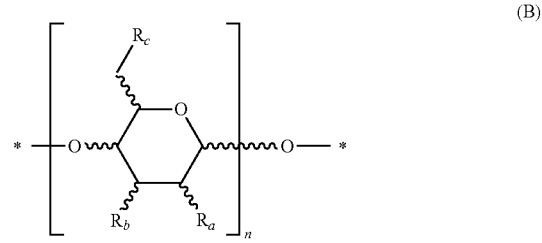

(B)

in which formula (B):
the $R_a$, $R_b$, $R_c$ radicals of each saccharide unit may be identical or different;
n is an integer greater than or equal to 2, particularly between 3 and 3000 inclusive, and more particularly between 5 and 2500, preferentially between 10 and 2300;
$R_a$, $R_b$, and $R_c$, which are identical or different, represent
i) a hydroxyl group, ii) a ($C_1$-$C_4$)alkoxy group, the alkyl group of which may be optionally substituted, especially with one or more hydroxyl groups, iii) a carboxyl group, and iv) an $NR_1R_2$ group, with $R_1$ and $R_2$ as defined above, in particular $R_1$ and $R_2$ are chosen from a hydrogen atom and —C(O)—$R'_1$ in which $R'_1$ is as defined above; preferably $R_1$ and $R_2$ represent i) a hydrogen atom or ii) —C(O)—$R'_1$ with $R'_1$ representing a ($C_1$-$C_4$)alkyl group such as methyl;

it being understood that at least one of the $R_a$, $R_b$, or $R_c$ radicals of at least one saccharide unit represents an $NR_1R_2$ group and that at least one of the $NR_1R_2$ groups of at least one saccharide unit represents an $NH_2$ group; preferably $R_a$ of at least one saccharide unit represents an $NR_1R_2$ group with $R_1$ which represents a hydrogen atom and $R_2$ is chosen from i) a hydrogen atom or ii) a —C(O)—$R'_1$ group, and $R_b$ and $R_c$ represent a hydroxyl group, it being understood that at least one of the $NR_1R_2$ groups of at least one saccharide unit represents an $NH_2$ group.

More particularly, the polysaccharide(s) with amine group (s) are of formula ($B_1$) below, and also the organic or mineral acid salts thereof, the α or β anomers thereof, the optical isomers thereof of L or D configuration, and the solvates thereof such as hydrates:

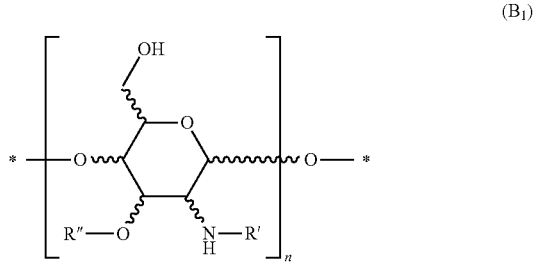

(B$_1$)

in which formula ($B_1$):

R' represents a hydrogen atom or a ($C_1$-$C_4$)alkylcarbonyl group such as acetyl $CH_3$—C(O)—;

R" represents a hydrogen atom or a ($C_1$-$C_4$)alkyl group optionally substituted with a carboxyl group such as —CH($CO_2$H)—$CH_3$;

n is an integer greater than or equal to 2, particularly between 3 and 3000 inclusive, more particularly between 5 and 2500, preferentially between 10 and 2300; it being understood that in the polysaccharide ($B_1$) at least one saccharide unit bears an $NH_2$ amino group and at least one other saccharide unit bears at least one N(H)—R' group with R' representing a ($C_1$-$C_4$)alkylcarbonyl group such as acetyl $CH_3$—C(O)—.

Preferably, the saccharide units of formula (B) or ($B_1$) are of D configuration, also referred to as D-glucopyran. The units of formula (B) or ($B_1$) are particularly of β (beta) anomeric configuration. According to one particular embodiment, the polysaccharides of the invention are chosen from the compounds of formula ($B_2$) below and also the organic or mineral acid salts thereof, and the solvates thereof such as hydrates:

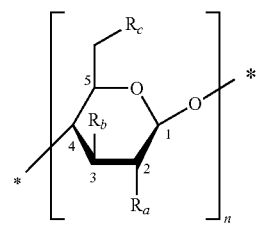

(B$_2$)

in which formula ($B_2$):

$R_a$, $R_b$, and $R_c$, are as defined for (B) above; and the $R_a$, $R_b$, $R_c$ radicals of each saccharide unit may be identical or different;

n is an integer greater than or equal to 2, particularly between 3 and 3000 inclusive, more particularly between 5 and 2500, preferentially between 10 and 2300; it being understood that in the polysaccharide ($B_2$) at least one of the $R_a$, $R_b$, or $R_c$ radicals of at least one saccharide unit represents an $NR_1R_2$ group and that at least one of the $NR_1R_2$ groups of at least one saccharide unit represents an $NH_2$ group; preferably at least one saccharide unit bears an $R_a$ amino $NH_2$ group and at least one other saccharide unit bears an $R_a$ group which represents —N(H)—R' with R' representing a ($C_1$-$C_4$)alkylcarbonyl group such as acetyl $CH_3$—C(O)—.

Preferentially, the polysaccharide(s) with amine group(s) are chosen from chitin and chitosan and their derivatives, preferably chitosan. Chitosan can be vegetable sourced (commercially known by the tradename of KIONUTRIME CSG, supplied by the company Kitozyme), or derived, for example, by treating the chitin shells of shrimp and other crustaceans with an alkaline substance, like sodium hydroxide.

More particularly, the polysaccharide(s) with amine group (s) are chosen from those of formula ($B_3$) below, and also the organic or mineral acid salts thereof, and the solvates thereof such as hydrates:

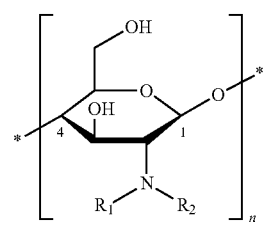

(B$_3$)

in which formula ($B_3$):

$R_1$ and $R_2$ are as defined in the formula (B), ($B_1$) or ($B_2$); and n is an integer greater than or equal to 2, particularly between 3 and 3000 inclusive, more particularly between 5 and 2500, preferentially between 10 and 2300; it being understood that in the polysaccharide of formula ($B_3$) at least one saccharide unit bears an $NH_2$ amino group and at least one other saccharide unit bears an N(H)—R' group with R' representing a ($C_1$-$C_4$)alkylcarbonyl group such as acetyl $CH_3$—C(O)—.

More particularly, the polysaccharide(s) with amine group(s) are chosen from chitosans of formula ($B_4$) below, and also the organic or mineral acid salts thereof, and the solvates thereof such as hydrates:

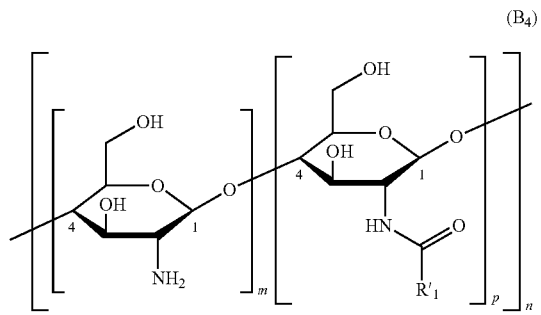

in which formula ($B_4$):

$R'_1$ representing a ($C_1$-$C_4$)alkyl group such as methyl; and n is an integer greater than or equal to 2, particularly between 3 and 3000 inclusive, more particularly between 5 and 2500, preferentially between 10 and 2300;

P is greater than 0 and ranges up to 0.5, preferably from 0.05 to 0.3, and better still from 0.1 to 0.20 such as 0.15 with m+p being equal to 1; it being understood that in the chitosan at least one saccharide unit bears an $NH_2$ amino group and at least one other saccharide unit bears an N(H)—$R'_1$ group with R' representing a ($C_1$-$C_4$)alkylcarbonyl group such as acetyl $CH_3$—C(O)—.

For example, when m=0.7, p=0.3 this means that 70% of the amine groups are free (unsubstituted) and 30% of the amino groups are N-alkyl($C_1$-$C_4$)carbonyl groups, in particular N-acetyl groups, corresponding to the chitosan of formula:

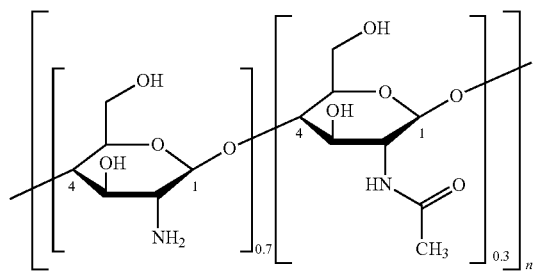

with n as defined above.

In some instances, the polysaccharide(s) with amine group(s) are chosen from chitosans, salicide using organic acid, preferentially using monocarboxylic acid of formula (I) as defined above or polycarboxylic acid of formula (II) as defined above, more preferentially salified using carboxylic acid of formula (I) such as lactic acid.

In some cases, the polysaccharide(s) with amine group(s) refers to a mixture of polysaccharide(s) with amine group(s), one of which is a chitosan or the organic or mineral acid salts thereof, preferably the salts thereof of an organic acid such as lactic acid, the α or β anomers thereof, the optical isomers thereof of L or D configuration, and the solvates thereof such as hydrates. Alternatively, the polysaccharide(s) with amine group(s) may relate to a single polysaccharide with amine group(s), in particular a mixture of chitosan or the organic or mineral salts thereof or more particularly the organic acid salts thereof such as the lactic acid salt thereof, the α or β anomers thereof, the optical isomers thereof of L or D configuration, and the solvates thereof such as hydrates.

According to at least one embodiment, the polysaccharide(s) with amine group(s) denotes a single polysaccharide with amine group(s), in particular a chitosan or the organic or mineral acid salts thereof or more particularly the organic acid salts thereof such as the lactic acid salt thereof, the α or β anomers thereof, the optical isomers thereof of L or D configuration, and the solvates thereof such as hydrates.

Ascorbic Acid

The hair treatment compositions include ascorbic acid, typically, in an amount ranging from about 0.01 to about 5 wt. %, based on the total weight of the hair treatment composition. For example, the total amount of ascorbic acid may be about 0.01 to about 5 wt. %, about 0.01 to about 4 wt. %, about 0.01 to about 3 wt. %, about 0.01 to about 2 wt. %, about 0.01 to about 1 wt. %; about 0.05 to about 5 wt. %, about 0.05 to about 4 wt. %, about 0.05 to about 3 wt. %, about 0.05 to about 2 wt. %, about 0.05 to about 1 wt. %, about 0.05 to about 0.5 wt. %; about 0.1 to about 5 wt. %, about 0.1 to about 4 wt. %, about 0.1 to about 3 wt. %, about 0.1 to about 2 wt. %, about 0.1 to about 1 wt. %; about 0.1 to about 0.5 wt. %, about 0.2 to about 5 wt. %, about 0.2 to about 4 wt. %, about 0.2 to about 3 wt. %, about 0.2 to about 2 wt. %, about 0.2 to about 1 wt. %, about 0.2 to about 0.5 wt. %, including all sub-ranges therebetween, based on the total weight of the hair treatment composition.

The ascorbic acid may be included in the hair treatment compositions in the form of an acid and/or a salt. For example, the ascorbic acid may be added to the hair treatment compositions in the form of a mineral ascorbate, such as sodium ascorbate, calcium ascorbate, magnesium ascorbate, potassium ascorbate, zinc ascorbate, molybdenum ascorbate, chromium ascorbate, and the like. In some instances, however, the ascorbic acid is added to the treatment composition in the form of an acid, such as L-ascorbic acid, D-ascorbic acid, or a mixture thereof.

Peroxide(s), Peroxo Compound(s), or Combination(s) Thereof

The hair treatment compositions include one or more peroxide(s), peroxo compound(s), or combination(s) thereof, typically, in an amount ranging from about 0.01 to about 5 wt. %, based on the total weight of the hair treatment composition. For example, the total amount of the one or more peroxide, peroxo compounds, or combinations thereof may be about 0.01 to about 5 wt. %, about 0.01 to about 4 wt. %, about 0.01 to about 3 wt. %, about 0.01 to about 2 wt. %, about 0.01 to about 1 wt. %, about 0.01 to about 0.5 wt. %; about 0.02 to about 5 wt. %, about 0.02 to about 4 wt. %, about 0.02 to about 3 wt. %, about 0.02 to about 2 wt. %, about 0.02 to about 1 wt. %, about 0.02 to about 0.5 wt. %; about 0.05 to about 5 wt. %, about 0.05 to about 4 wt. %, about 0.05 to about 3 wt. %, about 0.05 to about 2 wt. %, about 0.05 to about 1 wt. %, about 0.05 to about 0.5 wt. %; about 0.1 to about 5 wt. %, about 0.1 to about 4 wt. %, about 0.1 to about 3 wt. %, about 0.1 to about 2 wt. %, about 0.1 to about 1 wt. %; about 0.2 to about 5 wt. %, about 0.2 to about 4 wt. %, about 0.2 to about 3 wt. %, about 0.2 to about 2 wt. %, about 0.2 to about 1 wt. %, including all sub-ranges therebetween, based on the total weight of the hair treatment composition.

The one or more peroxides, peroxo compounds, or combinations thereof included in the hair treatment composition may be in the form of a metal peroxide, organic peroxide, peroxide acid or the like. For example, at least one of the peroxides and the peroxo compounds may be chosen from inorganic peroxides and peroxo compounds such as peroxides of alkali metals and alkaline earth metals, for example, calcium peroxide, urea-peroxide, sodium peroxoborates, sodium carbonate peroxohydrate, peroxodisulfate salts, calcium peroxide, sodium peroxide, and potassium superoxide, and combinations thereof. The peroxides or peroxo compounds may also be chosen from organic peroxides such as dioxirane, peroxides, alkyl-$C_{1-6}$, benzoyl peroxide, peroxo carboxylates ($C_1$-$C_6$) alkyl peroxides, bis (tri) ($C_1$-$C_6$) alkylsilyl peroxide such as bis (trimethylsilyl) alkyl peroxydicarbonates-$C_6$, sodium nonanoyloxybenzene sulfonate, and combinations thereof. In some instances, the one or more peroxide(s), peroxo compound(s), or combination(s) thereof comprises or consists of hydrogen peroxide.

Additional Acid(s) Other than Ascorbic Acid

The hair treatment compositions may optionally include one or more acids other than ascorbic acid. The acid(s) other than ascorbic acid, if present in the hair treatment composition, may be in an amount of about 0.01 to about 5 wt. %, based on the total weight of the hair treatment composition. For example, the total amount of acid(s) other than ascorbic acid may be about 0.01 to about 5 wt. %, about 0.01 to about 4 wt. %, about 0.01 to about 3 wt. %, about 0.01 to about 2 wt. %, about 0.01 to about 1 wt. %; about 0.05 to about 5 wt. %, about 0.05 to about 4 wt. %, about 0.05 to about 3 wt. %, about 0.05 to about 2 wt. %, about 0.05 to about 1 wt. %; about 0.1 to about 5 wt. %, about 0.1 to about 4 wt. %, about 0.1 to about 3 wt. %, about 0.1 to about 2 wt. %, about 0.1 to about 1 wt. %; about 0.2 to about 5 wt. %, about 0.2 to about 4 wt. %, about 0.2 to about 3 wt. %, about 0.2 to about 2 wt. %, about 0.2 to about 1 wt. %, including all sub-ranges therebetween, based on the total weight of the hair treatment composition.

The acid(s) other than ascorbic acid are chosen from non-polymeric acids having a structure that is linear, aromatic, or phenolic. In some instances, the acid(s) other than ascorbic acid may include or be chosen from tannic acid, caffeic acid, acetic acid, citric acid, gallic acid, and mixtures thereof.

Additionally, the acid(s) other than ascorbic acid may be chosen from carboxylic acids, fatty acids, and mixtures thereof. A non-polymeric mono, di, and/or tricarboxylic acid is an organic compound having one (mono), two (di), or three (tri) carboxylic acid groups (—COOH). The non-polymeric mono, di, and tricarboxylic acids, and/or salts thereof, typically have a molecular weight of less than about 500 g/mol, less than about 400 g/mol, or less than about 300 g/mol.

Non-limiting examples of monocarboxylic acids, or salts thereof, include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and a mixture thereof. In some cases, the hair treatment compositions include at least lactic acid and/or a salt thereof.

Non-limiting examples of dicarboxylic acids and/or salts thereof include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, a salt thereof, and a mixture thereof. In some cases, the hair treatment compositions include oxalic acid, malonic acid, malic acid, maleic acid, a salt thereof, or a mixture thereof.

Non-limiting examples of tricarboxylic acids and salts thereof include citric acid, isocitric acid, aconitric acid, propane-1,2,3-tricarboxylic acid, benzene-1,3,5-tricarboxylic acid, a salt thereof, and a mixture thereof. In some instances, the hair treatment compositions include at least citric acid and/or a salt thereof.

In some cases, the hair treatment compositions include at least one or more dicaboxylic acids, and/or a salt thereof, in particular, oxalic acid, malonic acid, malic acid, maleic acid, a salt thereof, or a mixture thereof. A particularly useful dicarboxylic acid is malonic acid and/or a salt thereof.

C5 to C6-Sugar Based Polysaccharide(s)

The hair treatment compositions may optionally include one or more C5 to C6-sugar based polysaccharides. The total amount of the one or more C5 to C6-sugar based polysaccharides can vary but is typically amount of about 0.1 to about 10 wt. %, based on the total weight of the hair treatment composition. For example, the total amount of C5 to C6-sugar based polysaccharides may be about 0.1 to about 10 wt. %, about 0.1 to about 8 wt. %, about 0.1 to about 5 wt. %, about 0.1 to about 3 wt. %; about 0.5 to about 10 wt. %, about 0.5 to about 8 wt. %, about 0.5 to about 5 wt. %, about 0.5 to about 3 wt. %; from about 0.8 to about 10 wt. %, about 0.8 to about 8 wt. %, about 0.8 to about 5 wt. %, about 0.8 to about 3 wt. %; or about 0.8 to about 2 wt. %, including all sub-ranges therebetween, based on the total weight of the hair treatment compositions.

In some particular embodiments, the one or more C5 to C6-sugar based polysaccharides according to the invention may especially be a fructosan chosen from inulin and derivatives thereof (especially dicarboxy and carboxymethyl inulins). Fructans or fructosans are oligosaccharides or polysaccharides comprising a sequence of anhydrofructose units optionally combined with several saccharide residues other than fructose. Fructans may be linear or branched. Fructans may be products obtained directly from a vegetable or microbial source or alternatively products whose chain length has been modified (increased or decreased) by fractionation, synthesis or hydrolysis, in particular enzymatic. Fructans generally have a degree of polymerization from 2 to about 1000 and, in some embodiments, from 2 to about 60.

Three groups of fructans are distinguished. The first group corresponds to products whose fructose units are for the most part linked via β(2,1) bonds. These are essentially linear fructans such as inulins. The second group also corresponds to linear fructoses, but the fructose units are essentially linked via β(2,6) bonds. These products are levans. The third group corresponds to mixed fructans, i.e. fructans containing β(2,6) and β(2,1) sequences. These are essentially branched fructans, such as graminans. Inulin is also referred to technically as Alantin, Fructosane, Synantherin, and Synanthrin Inulin may be obtained, for example, from chicory, dahlia or Jerusalem artichoke, in some embodiments, from chicory. Inulin is the polysaccharide that conforms to the following structure:

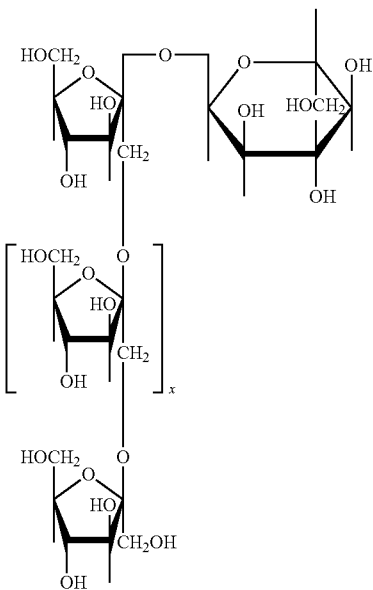

In particular, the polysaccharide, especially the inulin, has a degree of polymerization from 2 to about 1000 and, in some instances, from 2 to about 60, and a degree of substitution of less than 2 on the basis of one fructose unit. The inulin used for this invention is represented, for example, by the products available under the tradename INUTEC H25P (CREACHEM), also sold under the name Beneo™ Inulin by the company Orafti, and under the name Frutafit® by the company Sensus.

Protein-Based Material(s)

The hair treatment compositions may optionally include one or more protein-based materials.

The total amount of the one or more protein-based materials can vary but is typically amount of about 0.0.05 to about 10 wt. %, based on the total weight of the hair treatment composition. For example, the total amount of protein-based materials may be about 0.0.05 to about 10 wt. %, about 0.1 to about 8 wt. %, about 0.1 to about 5 wt. %, about 0.1 to about 3 wt. %; about 0.15 to about 10 wt. %, about 0.2 to about 8 wt. %, about 0.2 to about 5 wt. %, about 0.2 to about 3 wt. %; or about 0.2 to about 2 wt. %, including all sub-ranges therebetween, based on the total weight of the hair treatment compositions.

In various embodiments, the one or more protein-based materials according to the invention may include keratin material (wool, bodily hair, etc.), silk proteins, and plant proteins (soybean, oat, wheat, etc. protein). They may also originate from keratin extracts or hydrolysates such as gelatin.

In some particular embodiments, the one or more protein-based materials according to the invention may especially be chosen from gelatin, Hydrolyzed wheat protein, Hydrolyzed soy protein, Hydrolyzed oat protein, Hydrolyzed rice protein, Hydrolzed vegetable protein, Hydrolyzed yeast protein, Whey protein and mixtures thereof.

Silicone(s)

The hair treatment compositions may optionally include one or more silicones. The total amount of the one or more silicones can vary but is typically from about 0.1 to about 15 wt. %, based on the total weight of the hair-treatment composition. For example, the total amount of the silicones may be from about 0.1 to about 15 wt. %, about 0.1 to about 12 wt. %, about 0.1 to about 10 wt. %, about 0.1 to about 8 wt. %, about 0.1 to about 6 wt. %, about 0.1 to about 5 wt. %; about 0.5 to about 15 wt. %, about 0.5 to about 12 wt. %, about 0.5 to about 10 wt. %, about 0.5 to about 8 wt. %, about 0.5 to about 6 wt. %, about 0.5 to about 5 wt. %; about 1 to about 15 wt. %, about 1 to about 12 wt. %, about 1 to about 10 wt. %, about 1 to about 8 wt. %, about 1 to about 6 wt. %, about 1 to about 5 wt. %; about 2 to about 15 wt. %, about 2 to about 12 wt. %, about 2 to about 10 wt. %, about 2 to about 8 wt. %, about 2 to about 6 wt. %, or about 2 to about 5 wt. %, including ranges and sub-ranges therebetween, based on the total weight of the hair-treatment compositions.

The silicones may be hydrophobic or, in some instances, be functionalized to be hydrophilic. Preferably, the silicones of the hair treatment compositions are amino functionalized silicone. The term "amino-functionalized silicone" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

While not wishing to be bound by any particular theory, it is believed that amino functional groups of the amino silicone polymers may, in some cases, undergo reactive synergies with the polysaccharides with amine group(s) such as chitosan. Non-limiting examples of amino silicone oils include amodimethicone, aminoethylaminopropyl dimethicone, aminopropyl dimethicone, and a mixture thereof. The subject matter of U.S. patent application Ser. No. 16/117, 549, including the disclosure regarding the polysaccharides with amine group(s), the silicone compounds, the emulsifiers, and monosaccharaides, is incorporated herein in its entirety for all purposes.

In some instances, the amino-functionalized silicones are selected from compounds of the following formula:

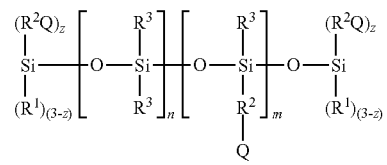

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from —$NR^4_2$ and —$NR^4(CH_2)_xNR^4_2$;

each $R^4$ is independently selected from a hydrogen and a $C_{1-4}$ alkyl group;

x is 2 to 6;
z is 0 or 1;
n is 25 to 3,000 (preferably, 25 to 2,000; more preferably, 25 to 1,000; most preferably 25 to 500); and
m is 0 to 3,000 (preferably, 0 to 2,000; more preferably, 0 to 1,000; most preferably, 0 to 100);
with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydoxy. Preferred $R^2$ divalent alkylene radicals include trimethylene, tetramethylene, pentamethylene, —$CH_2CH(CH_3)CH_2$— and —$CH_2CH_2CH(CH_3)$ $CH_2$—. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicone has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds having a structure in accordance with the following formula:

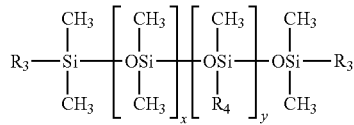

wherein $R_3$ is hydroxyl or $OR_5R_5$ is a $C_1$ to $C_4$ alkyl group, $R_4$ is a group with a structure according to the following formula:

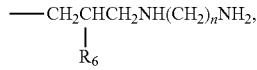

wherein $R_6$ is a $C_1$ to $C_4$ alkyl, n is a 1 to 4, x is the same as "n" described above, and y is the same as "m" described above.

Non-limiting examples of amino-functionalized silicones include bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is $OCH_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [(methoxydimethylsilyl)oxy]-terminated." Bis-hydroxy/methoxy amodimethicone is commercially available under the tradename DOWSIL AP-8087 FLUID from The Dow Chemical Company.

The silicone of the hair treatment composition may, in some instances, include polydiorganosiloxanes, e.g., polydimethylsiloxanes having the CTFA designation dimethicone. Additional silicones that may be suitable for the hair treatment compositions include (particularly for shampoos and conditioners) polydimethyl siloxanes having hydroxyl end groups, which have the CTFA designation dimethiconol. Silicone gums may, in some instances, be included in the hair treatment compositions, such as those having a slight degree of cross-linking. Non-limiting examples of silicone gums that may, optionally, be included are described in WO 96/31188, which is incorporated herein by reference for all purposes.

The silicone(s) may have a viscosity of at least 10,000 cst, such as at least 50,000 cst, at least 100,000 cst, at least 200,000 cst, at least 400,000 cst, at least 800,000 cst, at least 1,000,000 cst, or at least 2,000,000 cst. Preferably the viscosity does not exceed $10^9$ cst for ease of formulation.

The hair treatment composition may include pre-formed emulsions of silicones, such as emulsions DC2-1766, DC2-1784, and microemulsions DC2-1865 and DC2-1870 from Dow Corning, or cross-linked silicone gums, such as DC X2-1787 or DC X2-1391 from Dow Corning.

Cationic Surfactant(s)

The hair treatment composition may optionally include one or more cationic surfactant(s). The amount of cationic surfactants, if present in the hair treatment composition, may be from about 0.1 to about 10 wt. %, about 0.1 to about 8 wt. %, about 0.1 to about 6 wt. %, about 0.1 to about 4 wt. %, about 0.1 to about 3 wt. %; about 1 to about 10 wt. %, about 1 to about 8 wt. %, about 1 to about 6 wt. %, about 1 to about 4 wt. %, about 1 to about 3 wt. %; about 1.5 to about 10 wt. %, about 1.5 to about 8 wt. %, about 1.5 to about 6 wt. %, about 1.5 to about 4 wt. %, about 1.5 to about 3 wt. %; about 2 to about 10 wt. %, about 2 to about 8 wt. %, about 2 to about 6 wt. %, about 2 to about 4 wt. %, about 2 to about 3 wt. %, including all ranges and sub-ranges therebetween, based on the total weight of the hair treatment composition.

The term "cationic surfactant" means a surfactant that may be positively charged when it is contained in the hair treatment compositions according to the disclosure. This surfactant may bear one or more positive permanent charges or may contain one or more functional groups that are cationizable in the hair treatment composition according to the disclosure.

The one or more cationic surfactants, if present, may include or be chosen from quaternary ammonium compounds, amidoamines, or a mixture thereof. Examples of cationic surfactants that may be suitable for the hair treatment composition include or may be chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, behenamidoethyldimethylamine, behenamidoethyldimethylamine, arachidamido-propyidiethylamine, arachidamidoethyidiethylamine, arachidamidoethyidimethylamine, and mixtures thereof.

Additional, non-limiting examples of cationic surfactants include: cetyl trimethyl ammonium chloride available, for example, with trade name CA-2350 from Nikko Chemicals and CTAC 30KC available from KCI, stearyl trimethyl ammonium chloride with trade name Arquad 18/50 available from Akzo Nobel, hydrogenated tallow alkyl trimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

Hydrophilically substituted cationic surfactants in which at least one of the substituents contain one or more aromatic, ether, ester, amido, or amino moieties present as substituents or as linkages in the chain may also be in the hair treatment composition. Non-limiting examples of hydrophilically substituted cationic surfactants that may be useful in the hair treatment compositions include the materials having the following INCI designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

In one embodiment, the hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, alkyl am idopropyl trimonium salt, polyoxyethylene alkyl ammonium salt, and mixtures thereof. For example, commercially available hydrophilically substituted cationic surfactants may include those under the following trade names; VARISOFT 110, VARISOFT PATC, VARIQUAT K1215 and 638 from Witco Chemical, ETHOQUAD 18/25, ETHOQUAD O/12PG, ETHOQUAD C/25, and ETHOQUAD S/25 from Akzo, DEHYQUART SP from Cognis, and MONAQUAT ISEIS, and MONAQUAT SL-5 available from Uniqema.

In certain instances, the cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.

In some cases, the cationic surfactant is selected from cetrimonium chloride, behentrimonium chloride, and mixtures thereof. Non-polymeric, mono-, di-, and/or tri-carboxylic acids may be used to "neutralize" the amidoamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with amidoamines such as, for example, stearamidopropyl dimethylamine.

Fatty Compound(s)

The hair treatment compositions may optionally include one or more fatty compounds. The amount of fatty compounds, if present in the hair treatment composition, may range from about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %; about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %; about 5 to about 20 wt. %, about 5 to about 18 wt. %, about 5 to about 16 wt. %, about 5 to about 14 wt. %, about 5 to about 12 wt. %, about 5 to about 10 wt. %, or about 5 to about 8 wt. %, including all ranges and sub-ranges therebetween, based on the total weight of the hair treatment composition.

Suitable fatty compounds, if present, include or may be chosen from oils, mineral oil, alkanes (paraffins), fatty alcohols, fatty acids, fatty alcohol derivatives, fatty acid derivatives, esters of fatty alcohols, hydroxy-substituted fatty acids, waxes, triglyceride compounds, lanolin, and a mixture thereof. In some instances, it may be preferable to include one or more fatty alcohols, such as those further discussed below.

Fatty Alcohols

Suitable fatty alcohols, if present, include those having a fatty group with a carbon chain of greater than 8 carbon atoms, 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Acid(s)

In some instances, the fatty compounds may be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

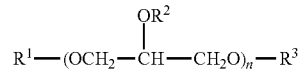

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Wax(es)

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof.

Oil(s)

In some instances, the fatty compounds may include or be chosen from one or more oil(s). Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Non-limiting examples of oils that may, optionally, be included in the hair treatment compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Cationic Polymer(s)

The hair treatment compositions may optionally include one or more cationic polymers. The amount of cationic polymers, if present in the hair treatment composition, may be from about 0.1 to about 10 wt. % of the total weight of the hair treatment composition. In some instances, the conditioning agents are in an amount ranging from about 0.1 to about 10 wt. %, about 0.1 to about 8 wt. %, about 0.1 to about 6 wt. %, about 0.1 to about 4 wt. %, about 0.1 to about 3 wt. %; about 1 to about 10 wt. %, about 1 to about 8 wt. %, about 1 to about 6 wt. %, about 1 to about 4 wt. %, about 1 to about 3 wt. %; about 1.5 to about 10 wt. %, about 1.5 to about 8 wt. %, about 1.5 to about 6 wt. %, about 1.5 to about 4 wt. %, about 1.5 to about 3 wt. %; about 2 to about 10 wt. %, about 2 to about 8 wt. %, about 2 to about 6 wt. %, about 2 to about 4 wt. %, about 2 to about 3 wt. %, including ranges and sub-ranges therebetween, based on the total weight of the hair treatment composition.

The cationic polymers can comprise mixtures of monomer units derived from amine- and/or quaternary ammonium-substituted monomer and/or compatible spacer monomers. Suitable cationic polymers include, for example: copolymers of 1-vinyl-2-pyrrolidine and 1-vinyl-3-methyl-imidazolium salt (e.g., chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other cationic polymers that may be used include polysaccharide polymers, such as cationic cellulose derivatives and cationic starch derivatives. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200. Additionally or alternatively, the cationic conditioning polymers may include or be chosen from cationic guar gum derivatives, such as guar hydroxypropyltrimonium chloride.

The hair treatment composition may include or be chosen from polyquaterniums. For example, the hair treatment composition may include Polyquaternium-1 (ethanol, 2,2', 2''-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), Polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), Polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (auaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quatemized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), Polyquaternium-47 (terpolymer of acrylic acid, methacrylamidopropyl trimethylammonium chloride, and methyl acrylate), and/or Polyquaternium-67.

In some instances, the hair treatment compositions of the instant disclosure include one or more cationic polymers selected from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. For example, the cationic polymer(s) may be selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, polyquaternium-67 and a mixture thereof. A combination of two or more polyquaterniums can be useful.

In one instance, the one or more cationic polymers is chosen from polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, and a mixture thereof.

According to another aspect of the disclosure, provided is a kit for treating hair. The kits may be used by hair-care professionals and salons for treating the hair of patrons or the kits may be purchased and used at home directly by consumers. The kits may include one or more compounds discussed with reference to the hair treatment composition.

The kits disclosed herein typically include:
(1) a first composition comprising one or more polysaccharides with amine group(s) and water;
(2) a second composition comprising up to 100 wt. % of ascorbic acid, based on the total weight of the second composition; and
(3) a third composition comprising a peroxide, a peroxo compounds, or a combination thereof,
    wherein the first composition, the second composition, and the third composition are separately contained.

The first composition may contain one or more polysaccharides with amine group(s) and water within a container. Preferably, the one or more polysaccharides with amine group(s) is solubilized within the water. The one or more polysaccharides with amine group(s) of the first composition may be those discussed above with reference to the hair treatment composition. The total amount of polysaccharides with amine group(s) present in the first composition may be about 0.1 to about 10 wt. %, about 0.1 to about 8 wt. %, about 0.1 to about 5 wt. %, about 0.1 to about 3 wt. %; about 0.5 to about 10 wt. %, about 0.5 to about 8 wt. %, about 0.5 to about 5 wt. %, about 0.5 to about 3 wt. %; from about 0.8 to about 10 wt. %, about 0.8 to about 8 wt. %, about 0.8 to about 5 wt. %, about 0.8 to about 3 wt. %; or about 0.8 to about 2 wt. %, including all sub-ranges therebetween, based on the total weight of the first composition.

The second composition may contain in a container up to 100 wt. % of ascorbic acid, based on the total weight of the second composition. For example, the composition may contain at least 80 wt. %, at least 85 wt. %, at least 90 wt. %, at least 92 wt. %, at least 94 wt. %, at least 96 wt. %, at least 98 wt. % or at least 99 wt. % of ascorbic acid, based on the total weight of the second composition. In some instances, the second composition consists of or consists essentially of ascorbic acid. As discussed above with reference to the hair treatment composition, the ascorbic acid may be in the form of an acid and/or a salt. Additionally or alternatively, the ascorbic acid may be L-ascorbic acid, D-ascorbic acid, or a mixture thereof.

The third composition may comprise a peroxide, a peroxo compound, or a combination thereof in a container. The peroxide and/or peroxo compound may be in the form of a solid or a liquid solution. The third composition may contain up to 100 wt. % of peroxide and/or peroxo compound, based on the total weight of the third composition. For example, the third composition may contain at least 80 wt. %, at least 85 wt. %, at least 90 wt. %, at least 92 wt. %, at least 94 wt. %, at least 96 wt. %, at least 98 wt. % or at least 99 wt. % of peroxide and/or peroxo compound, based on the total weight of the third composition. The peroxide and/or peroxo compound may be chosen from peroxides and/or peroxo compounds disclosed above with reference to the hair treatment composition. In one instance, the first, second, and/or third composition is applied onto hair immediately after at least one of: chemical treatment of the hair, the hair has been subjected to chemical damage, the hair has been subjected to mechanical damage, the hair has been subjected to heat damage, or the hair has been subjected to environmental damage.

In accordance with a further aspect of the disclosure, methods are provided for using the hair treatment compositions and/or kits disclosed herein. The methods preferably improve the color retention of artificially colored hair. For example, the method may include applying the second composition, discussed below, to hair that has been artificially colored hair with at least one die, pigment, or a combination thereof, preferably within 1 hour of artificially coloring such hair to improve the color retention of the artificially colored hair. The methods may use one or more compounds and/or compositions discussed herein with reference to the hair treatment composition and/or the kits. The methods for treating hair typically include:
i) obtaining a first composition comprising one or more polysaccharides with amine group(s) and water;
ii) adding ascorbic acid and one or more peroxides, peroxo compounds, or combinations thereof to the first composition to obtain a second composition;
iii) applying the second composition to hair; and
iv) heating the hair, which has the second composition applied thereto, to a temperature above 25° C.

In some instances, to reduce the damage to hair and/or improve the hair, the second composition may be applied onto hair immediately after at least one of: chemical treatment of the hair, the hair has been subjected to chemical damage, the hair has been subjected to mechanical damage, the hair has been subjected to heat damage, or the hair has been subjected to environmental damage. The benefits provided by the hair treatment compositions or kits disclosed herein may be enhanced by the method for using such hair treatment compositions or kits. For example, the method may include applying heat at a temperature of about 30° C. to about 80° C. to hair, which has been applied with a composition comprising polysaccharide(s) with amine group(s), ascorbic acid, and one or more peroxides, peroxo compounds, or combinations thereof.

The hair may be heated using heating device including, but not limited to, hair blow dryers, flat iron, heating hoods, curling iron, etc. Preferably the hair is heated at a temperature of 25° C. or more, such as at a temperature of 25° C. to 250° C., 30° C. to 230° C., 30° C. to 200° C., 30° C. to 150° C., 30° C. to 100° C., 30° C. to 80° C., or 30° C. to 60° C. In some instances, the hair may be heated, optionally using a hair blow drying, at a temperature of about 32° C. to about 70° C., about 34° C. to about 60° C., about 36° C. to about 60° C., about 38° C. to about 60° C., about 40° C. to about 60° C., about 42° C. to about 60° C., about 44° C. to about 60° C., about 46° C. to about 60° C., about 48° C. to about 60° C., or about 50° C. to about 60° C. In at least one embodiment, the temperature range is from about 30 C to 80 C using a heating device such as hair blow dryer. The hair may be heated for a period of about 1 minute to about 1 hour, preferably for about 5 minutes to 1 hour, preferably for about 5 minutes to about 55 minutes, preferably for about 10 minute to about 55 minutes, or preferably for about 10 minute to about 50 minutes. The methods may, in some instances, heat the hair to a temperature above 25° C., e.g., 28° C. or more, 30° C. or more, 32° C. or more, 34° C. or more, 36° C. or more, 38° C. or more, or 40° C. or more. After treating the hair with the hair treatment composition, the hair may be shaped or styled using a mechanical device such as a comb, brush, and/or other similar shaping tool and with or without heat.

As mentioned above, the method may include one or more compounds and/or compositions discussed herein with reference to the hair treatment composition and/or the kits. For example, the first composition may comprise water and one or more polysaccharides with amine group(s) chosen from the compounds discussed above. Similarly, the ascorbic acid and the one or more peroxide(s), peroxo compound(s), or combination(s) thereof, which are added to the first composition to obtain the second composition, may be chosen from the ascorbic acid and peroxides, peroxo compounds, or combinations thereof discussed herein. The ascorbic acid and the one or more peroxide(s) and/or peroxo compounds may be contained in the same container prior to adding into the first composition comprising one or more polysaccharides with amine group(s) if the ascorbic acid and/or peroxides do not react or degrade. For example, optionally, the ascorbic acid and the one or more peroxides and/or peroxo compounds may be in a dry solid form, such that the ascorbic acid and the one or more peroxides and/or peroxo compounds do not react with each other.

The methods may optionally include adding one or more acids other than ascorbic acid to the first composition, the second composition, or to both the first and second compositions. Preferably, the second composition has a pH of about 2 to about 6, e.g., after the ascorbic acid and one or more peroxides and/or peroxo compounds have been mixed into the first composition. Additionally or alternatively, the first and/or second composition of the method may be formulated such that an emulsion is not produced.

EMBODIMENTS OF THE DISCLOSURE

In certain embodiments, the methods for treating hair of the instant disclosure include:
  obtaining a first composition comprising one or more polysaccharides with amine group(s) and water, the one or more polysaccharides preferably being selected from polyhexosamines, organic or mineral acid salts thereof, α or β anomers thereof, isomers thereof of L or D configuration, and solvates/hydrates thereof, and more preferably being selected from chitosan;
  adding ascorbic acid and one or more peroxides, peroxo compounds, or combinations thereof to the first composition to obtain a second composition preferably having a pH of about 2 to about 6 and more preferably having a pH of about 3 to about 4, wherein the one or more peroxides, peroxo compounds, or combinations thereof are chosen from calcium peroxide, urea-peroxide, sodium peroxoborates, sodium carbonate peroxohydrate, peroxodisulfate salts, calcium peroxide, sodium peroxide, and potassium superoxide, dioxirane, peroxides, alkyl-$C_{1-6}$, benzoyl peroxide, peroxo carboxylates ($C_1$-$C_6$) alkyl peroxides, bis (tri) ($C_1$-$C_6$) alkylsilyl peroxide such as bis (trimethylsilyl) alkyl peroxydicarbonates-$C_6$, sodium nonanoyloxybenzene sulfonate, hydrogen peroxide, and combinations thereof;
  optionally, adding one or more acids other than ascorbic acid to the first composition, the second composition, or to both the first and the second compositions, the one or more acids other than ascorbic acid being chosen from non-polymeric acids having a structure that is linear, aromatic, or phenolic, such as tannic acid, caffeic acid, acetic acid, citric acid, gallic acid, and mixtures thereof;
  optionally, adding one or more silicones to the first composition, the second composition, or to both the first and the second compositions, the one or more silicones preferably being chosen from amino functionalized silicones containing at least one primary amino, secondary amino, tertiary amino and/or quaternary ammonium group, including, e.g., bis-hydroxy/methoxy amodimethicones, bis-cetearyl amodimethicone, amodimethicone, bis($C_{13}$-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof;
  optionally, adding one or more cationic surfactants to the first composition, the second composition, or to both the first and the second compositions, the one or more cationic surfactants preferably being chosen from quaternary ammonium compounds, amidoamines, or a mixture thereof, such as those chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof;

optionally, adding one or more fatty compounds to the first composition, the second composition, or to both the first and the second compositions, the one or more fatty compounds including, e.g., those chosen from oils, mineral oil, alkanes (paraffins), fatty alcohols, fatty acids, fatty alcohol derivatives, fatty acid derivatives, esters of fatty alcohols, hydroxy-substituted fatty acids, waxes, triglyceride compounds, lanolin, and a mixture thereof;

optionally, adding one or more cationic polymer to the first composition, the second composition, or to both the first and the second compositions, the one or more cationic polymer preferably being derived from amine- and/or quaternary ammonium-substituted monomer and/or compatible spacer monomers, such as polyquaternium compounds;

optionally, adding one or more C5 to C6-sugar based polysaccharide to the first composition, the second composition, or to both the first and the second composition, the one or more C5 to C6-sugar based polysaccharide comprising at least one of fructose-based polysaccharide (fructosan) and inulin;

optionally, adding one or more protein-based material to the first composition, the second composition, or to both the first and the second composition;

applying the second composition to hair, e.g., immediately after at least one of: chemical treatment of the hair, the hair has been subjected to chemical damage, the hair has been subjected to mechanical damage, the hair has been subjected to heat damage, or the hair has been subjected to environmental damage;

heating the hair, which has the second composition applied thereto, to a temperature above 25° C., such as at a temperature of 30° C. to 230° C., preferably at a temperature of 30° C. to 200° C., preferably at temperature of 30° C. to 150°, more preferably at temperature of about 30° C. to about 80° C., e.g., using a heating device chosen from a blow dryer, a flat iron, a heating hood, and a curling iron, preferably using a hair blow dryer; and optionally, shaping or styling the hair suing a using a mechanical device such as a comb, brush or other similar shaping tools and with or without heat.

In further embodiments, the kits of the instant disclosure include:

a first composition comprising one or more polysaccharides with amine group(s) and water, the one or more polysaccharides preferably being selected from polyhexosamines, organic or mineral acid salts thereof, α or β anomers thereof, isomers thereof of L or D configuration, and solvates/hydrates thereof, and more preferably being selected from chitosan;

a second composition comprising up to 100 wt. % of ascorbic acid, wherein the weight percentage of ascorbic acid is based on the total weight of the second composition;

a third composition comprising a peroxide, a peroxo compound, or a combination thereof chosen from calcium peroxide, urea-peroxide, sodium peroxoborates, sodium carbonate peroxohydrate, peroxodisulfate salts, calcium peroxide, sodium peroxide, and potassium superoxide, dioxirane, peroxides, alkyl-$C_{1-6}$, benzoyl peroxide, peroxo carboxylates ($C_1$-$C_6$) alkyl peroxides, bis (tri) ($C_1$-$C_6$) alkylsilyl peroxide such as bis (trim-ethylsilyl) alkyl peroxydicarbonates-$C_6$, sodium nonanoyloxybenzene sulfonate, and combinations thereof, such as hydrogen peroxide;

optionally, at least one of the first composition, the second composition, and the third compositions includes one or more acids other than ascorbic acid, preferably those chosen from non-polymeric acids having a structure that is linear, aromatic, or phenolic, such as tannic acid, caffeic acid, acetic acid, citric acid, gallic acid, and mixtures thereof;

optionally, at least one of the first composition, the second composition, and the third compositions includes one or more silicones preferably being chosen from amino functionalized silicones containing at least one primary amino, secondary amino, tertiary amino and/or quaternary ammonium group, including, e.g., bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof;

optionally, at least one of the first composition, the second composition, and the third compositions includes one or more cationic surfactants preferably being chosen from quaternary ammonium compounds, amidoamines, or a mixture thereof, such as those chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof;

optionally, at least one of the first composition, the second composition, and the third compositions includes one or more fatty compounds including, e.g., those chosen from oils, mineral oil, alkanes (paraffins), fatty alcohols, fatty acids, fatty alcohol derivatives, fatty acid derivatives, esters of fatty alcohols, hydroxy-substituted fatty acids, waxes, triglyceride compounds, lanolin, and a mixture thereof;

optionally, at least one of the first composition, the second composition, and the third compositions includes one or more cationic polymers preferably being derived from amine- and/or quaternary ammonium-substituted monomer and/or compatible spacer monomers, such as polyquaternium compounds;

optionally, at least one of the first composition, the second composition, and the third compositions includes one or more C5 to C6-sugar based polysaccharide, the one or more C5 to C6-sugar based polysaccharide comprising at least one of fructose-based polysaccharide (fructosan) and inulin;

optionally, at least one of the first composition, the second composition, and the third compositions includes one or more protein-based material; and wherein the first composition, the second composition, and the third composition are separately contained.

In yet further embodiments, the hair treatment compositions of the instant disclosure include:
- one or more polysaccharides with amine group(s), preferably in an amount of about 0.1 to about 10 wt. %, and more preferably about 0.5 to about 5%, wherein the one or more polysaccharides are preferably selected from polyhexosamines, organic or mineral acid salts thereof, α or β anomers thereof, isomers thereof of L or D configuration, and solvates/hydrates thereof, and are more preferably selected from chitosan;
- ascorbic acid, preferably in an amount of about 0.01 to about 5 wt. %, and more preferably about 0.1 to about 2 wt. %;
- one or more peroxides, peroxo compounds, or combinations thereof preferably in an amount of about 0.01 to about 5 wt. %, and more preferably about 0.02 to about 2 wt. %, wherein the one or more peroxides, peroxo compounds, or combinations thereof are chosen from calcium peroxide, urea-peroxide, sodium peroxoborates, sodium carbonate peroxohydrate, peroxodisulfate salts, calcium peroxide, sodium peroxide, and potassium superoxide, dioxirane, peroxides, alkyl-$C_{1-6}$, benzoyl peroxide, peroxo carboxylates ($C_1$-$C_6$) alkyl peroxides, bis (tri) ($C_1$-$C_6$) alkylsilyl peroxide such as bis (trimethylsilyl) alkyl peroxydicarbonates-$C_6$, sodium nonanoyloxybenzene sulfonate, and combinations thereof, such as hydrogen peroxide;
- optionally, one or more acids other than ascorbic acid, including those chosen from non-polymeric acids having a structure that is linear, aromatic, or phenolic, such as tannic acid, caffeic acid, acetic acid, citric acid, gallic acid, and mixtures thereof; and
- optionally, one or more silicones, such as amino functionalized silicones containing at least one primary amino, secondary amino, tertiary amino and/or quaternary ammonium group including, e.g., bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof;
- optionally, one or more cationic surfactants chosen from quaternary ammonium compounds, amidoamines, or a mixture thereof, such as those chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.
- optionally, one or more fatty compounds including, e.g., those chosen from oils, mineral oil, alkanes (paraffins), fatty alcohols, fatty acids, fatty alcohol derivatives, fatty acid derivatives, esters of fatty alcohols, hydroxy-substituted fatty acids, waxes, triglyceride compounds, lanolin, and a mixture thereof;
- optionally, one or more cationic polymer preferably derived from amine- and/or quaternary ammonium-substituted monomer and/or compatible spacer monomers, such as polyquaternium compounds;
- water, wherein the hair treatment composition has a pH of about 2 to about 6 and preferably about 3 to about 4, and all amounts are by weight of the hair treatment composition.

In additional embodiments, a method for improving the color retention of artificially colored hair includes:
- obtaining a first composition comprising one or more polysaccharide with amine group(s) and water, wherein the one or more polysaccharides are preferably selected from polyhexosamines, organic or mineral acid salts thereof, α or β anomers thereof, isomers thereof of L or D configuration, and solvates/hydrates thereof, and are more preferably selected from chitosan;
- adding ascorbic acid and one or more peroxides, peroxo compounds, or combinations thereof to the first composition to obtain a second composition, the one or more peroxides, peroxo compounds, or combinations thereof being chosen from calcium peroxide, urea-peroxide, sodium peroxoborates, sodium carbonate peroxohydrate, peroxodisulfate salts, calcium peroxide, sodium peroxide, and potassium superoxide, dioxirane, peroxides, alkyl-$C_{1-6}$, benzoyl peroxide, peroxo carboxylates ($C_1$-$C_6$) alkyl peroxides, bis (tri) ($C_1$-$C_6$) alkylsilyl peroxide such as bis (trimethylsilyl) alkyl peroxydicarbonates-$C_6$, sodium nonanoyloxybenzene sulfonate, and combinations thereof, such as hydrogen peroxide; and
- applying the second composition to the artificially colored hair, wherein the hair is preferably artificially colored prior to applying the second composition to the artificially colored hair with at least one die, pigment, or a combination thereof, the second composition be preferably applied within 1 hour of artificially coloring the hair;
- optionally, heating the hair, which has the second composition applied thereto, to a temperature above 25° C., preferably to a temperature of 30° C. to 230° C., preferably at a temperature of 30° C. to 200° C., preferably at temperature of 30° C. to 150°, more preferably at temperature of about 30° C. to about 80° C., e.g., using a heating device chosen from a blow dryer, a flat iron, a heating hood, and a curling iron, preferably using a hair blow dryer; and
- optionally, shaping or styling the hair suing a using a mechanical device such as a comb, brush or other similar shaping tools and with or without heat.

EXAMPLES

The following non-limiting examples are provided primarily for the purposes of elucidating the benefits and properties achieved by aspects of the invention.

Example 1

Five non-limiting, exemplary hair treatment compositions (Example Formulas A-E) were prepared according to aspects of the invention. Three comparative hair treatment compositions (Comparative Formulas F-H) were prepared according to processes similar to those used for preparing Example Formulas A-E. A summary of the compositions of Example Formulas A-E and Comparative Formulas F-H is provided below in Table 1.

TABLE 1

| US INCI Name | Example Formula A | Example Formula B | Example Formula C | Example Formula D | Example Formula E | Comparative Formula F | Comparative Formula G | Comparative Formula H |
|---|---|---|---|---|---|---|---|---|
| a) Chitosan | 1 | 1 | 1 | 1 | 1 | 1 | 1 | |
| b) Ascorbic Acid | 0.12 | 0.12 | 0.12 | 0.12 | 0.12 | 0.12 | | |
| c) Hydrogen Peroxide | 0.068 | 0.068 | 0.068 | 0.068 | 0.068 | | | |
| e) Tannic Acid | 0.5 | | | | | | | |
| Citric Acid | | | | 0.5 | | | | |
| Gallic Acid | | | 0.5 | | | | | |
| Caffeic Acid | | 0.5 | | | | | | |
| Acetic Acid | | Q.S. to a pH of 3.3 | | | | | Q.S. to a pH of 3.5 | |
| d) water | | | | | Q.S. to 100 | | | |

Example 2

Example Formulas D and E and Comparative Formulas F and G were each applied to hair swatches to assess the pigment retention due to the application of such compositions. The hair swatches were commercially obtained and initially had a platinum bleach color. In order to assess the pigment retention on the hair swatches by the foregoing compositions, carbon black pigment was incorporated into the hair swatches. A control was prepared by applying carbon black pigment to hair swatches without applying a hair treatment composition thereafter.

The hair swatches were sprayed with 0.8 g of carbon black pigment per g of hair. The carbon black pigment was then spread uniformly through the hair swatches using hands and an applicator brush. The hair swatches were subsequently rough blow dried by holding the swatch in front of the blow dryer without using a brush or manually manipulating the hair of the hair swatch.

Hair swatches were then sprayed with 0.8 g per g of hair of one of the hair treatment compositions of Example Formulas D and E and Comparative Formulas F and G. The hair treatment compositions were spread uniformly through the hair swatches using hands and an applicator brush. The hair swatches receiving the foregoing compositions were then rough blow dried by holding the swatch in front of the blow dryer without using a brush or manually manipulating the hair of the hair swatch.

A ColorShot MultiSpectral device, produced by Newtone Technologies, was used to evaluate the color retention of treated swatches as a function of washing using CIE L*a*b* coordinates. ΔE is used to describe the color difference, where a greater ΔE value represents increased removal of color or decreased retention of color. ΔE is defined by the following equation:

$$\Delta E = \sqrt{(L^* - L_0^*)^2 + (a^* - a_0^*)^2 + (b^* - b_0^*)^2}$$

where $L^*$, $a^*$, and $b^*$ represent the values measured on the hair treated with carbon black and/or the treatment composition and $L_0^*$, $a_0^*$, and $b_0^*$ represent the values measured on the hair after washes.

Measurements were taken immediately after completion of the rough blow drying, after a first wash, after a second washes, after a sixth wash, and after an eleventh wash. Example Formulas D and E and Comparative Formulas F and G all provided improved color retention in comparison to the control. While not being limited by any particular theory, the inventors believe that the chitosan facilitated the retention of the carbon black pigment incorporated into the hair swatches.

Example 3

Example Formulas D and E, Comparative Formulas F and G, and a Control were applied to hair swatches to assess sensorial effect of such compositions on the hair swatches. The Control was distilled water having a neutral pH.

A total of three treatments of each of the compositions were applied to each hair swatch with three washes occurring between each of the treatments. Prior to the first treatment, the hair swatches were washed with shampoo and then dried by way of dabbing using a paper towel. The hair swatches were then sprayed with 0.4 g of the foregoing compositions per g of hair of the hair swatch. The compositions were spread uniformly through the hair swatches using hands and an applicator brush. The hair swatches were subsequently rough blow dried until they became about 80% dry. The hair swatches were then brush blow dried for 20 passes each. Brush blow dying includes brushing the hair of the hair swatches with long brush strokes along the whole length of the hair while simultaneously blow drying the hair swatches in coordination with the brush strokes. Brush blow drying typically increases smoothness and alignment of the hair of the hair swatches in comparison to rough blow drying. The hair swatches were subsequently washed three times to simulate a week of washes in between usage of the foregoing compositions by a user.

A second treatment of the foregoing compositions was applied to the respective hair swatches. As described above, the hair swatches were sprayed with 0.4 g of the foregoing compositions per g of hair of the hair swatch, then rough blow dried, and subsequently brush blow dried. The hair swatches were subsequently washed three times prior to application of the third treatment.

A third treatment of the foregoing compositions was applied to the respective hair swatches. Similar to the application of the first and second treatments, the hair swatches were sprayed with 0.4 g of the foregoing compositions per g of hair of the hair swatch. The hair swatches were then rough blow dried and brush blow dried. The hair swatches were then assessed to determine the sensorial effects of Example Formulas D and E, Comparative Formulas F and G, and the Control.

Comparative Formula F showed improved visual and tactile smoothness, dry ends, suppleness and coating compared to the Control. Example Formula E showed improved tactile smoothness, dry ends, strength, and alignment compared to the Control. Example Formula D showed improved tactile smoothness and ease of combing compared to the Control.

Example 4

The adhesion and cohesion properties of Example Formulas D and E were assessed in comparison to Comparative Formulas G and F. Specifically, Example Formulas D and E and Comparative Formulas G and F were each applied to two sets of glass slides. The first set of glass slides were allowed to dry overnight, while the second set of glass slides were dried in an oven at 50° C. for 40 minutes. Drying the second set of glass sides in an oven at 50° C. for 40 minutes mimics the temperature of a blow dryer on a medium setting.

After drying, the glass slides were submerged in a 1 wt. % shampoo solution. The adhesion of Example Formulas D and E and Comparative Formulas G and F to the glass films were observed and recorded after initial submersion into the 1 wt. % shampoo solution and after 1 hr, 24 hrs, and 72 hrs after submersion into the 1 wt. % shampoo solution. The level of adhesion was assessed based on the extent to which the film detached from the surface of the glass film. The level of cohesion was assessed based on the integrity of the film and how quickly the film disintegrates causing haziness within the 1 wt. % shampoo solution.

Example Formulas D and E both provided superior adhesion and cohesion compared to Comparative Formulas F and G, with Example Formula D exhibiting better adhesion and cohesion properties than Example Formula E. Furthermore, the compositions that were applied to the set of glass films, which were dried in the oven, exhibited better adhesion and cohesion than the compositions on the set of glass films that dried by air. Additionally, Example Formulas D and E created an adhesive and cohesive film, which translates to wash-off resistance and lastingness on hair.

Example 5

The denaturation temperature of the compositions of Example Formula E and Comparative Formulas G and F were assessed to determine the extent of hair repair occurring on hair swatches. Specifically, a higher denaturation temperature was indicative of higher treatment efficacy. The compositions of Example Formula E and Comparative Formulas G and F were each separately mixed for 5 minutes before being applied to two sets of hair swatches. The first set of hair swatches received one application of compositions of Example Formula E and Comparative Formulas G and F. The second set of hair swatches received three applications of compositions of Example Formula E and Comparative Formulas G and F.

The denaturation temperature of Example Formula E was 145.3° C. and 145.4° C. for the hair swatches receiving 1 application and 3 applications, respectively, of the foregoing composition. The denaturation temperature of Comparative Formula F was 141.8° C. for both hair swatches receiving 1 application and 3 applications of the foregoing composition. The denaturation temperature of Comparative Formula G were 139.5° C. and 139° C. for the hair swatches receiving 1 application and 3 applications, respectively, of the foregoing composition. Additionally, it was observed that the denaturation temperature for Example Formula E increased significantly when mixed for 1 minute and applied 3 times as compared to being mixed for 1 minute and applied only one time.

The terms "comprising," "having," and "including" are used in their open, non-limiting sense. The terms "a" and "the" are understood to encompass the plural as well as the singular. The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated. All ranges and values disclosed herein are inclusive and combinable. The expression "inclusive" for a range of concentrations means that the limits of the range are included in the defined interval. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the compositions. Nonetheless, the compositions may include less than about 2 wt. %, less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included. The salts referred to throughout the disclosure may include salts having a counter-ion such as an alkali metal, alkaline earth metal, or ammonium counter-ion. This list of counter-ions, however, is non-limiting.

"Volatile", as used herein, means having a flash point of less than about 100° C. "Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A method for treating hair comprising:
   (i) obtaining a first composition comprising chitosan;
   (ii) adding ascorbic acid and one or more peroxides to the first composition to obtain a second composition; and
   (iii) applying the second composition to hair, wherein the second composition has a pH of about 2 to about 6 and comprises:
      (a) about 0.1 to about 10 wt. % of the chitosan;
      (b) about 0.01 to about 5 wt. % of ascorbic acid;
      (c) about 0.01 to about 5 wt. % of the one or more peroxides;
      (d) about 60 to about 99 wt. % of water; and
      (e) optionally, about 0.1 to about 5 wt. % of one or more acids selected from tannic acid, caffeic acid, acetic acid, citric acid, gallic acid, or mixtures thereof;
      wherein the weight percentages are based on a total weight of the second composition.

2. The method of claim 1, further comprising heating the hair, which has the second composition applied thereto, to a temperature of above 25° C.

3. The method of claim 1, wherein the pH of the second composition is about 2.5 to about 5.

4. The method of claim 1, wherein the second composition comprises the one or more acids of (e).

5. The method of claim 4, wherein the second composition comprises tannic acid.

6. The method of claim 4, wherein the second composition comprises caffeic acid.

7. The method of claim 4, wherein the second composition comprises acetic acid.

8. The method of claim 4, wherein the second composition comprises citric acid.

9. The method of claim 4, wherein the second composition comprises gallic acid.

10. The method of claim 4 comprising heating the hair to a temperature of 30° C. to 200° C.

11. The method of claim 10, wherein the heating is carried out with a blow dryer, a flat iron, a heating hood, or a curling iron.

12. The method of claim 4, wherein the one or more peroxides is hydrogen peroxide.

13. The method of claim 4, wherein the second composition comprises:
   (a) about 0.1 to about 10 wt. % chitosan;
   (b) about 0.01 to about 5 wt. % of ascorbic acid;
   (c) about 0.01 to about 5 wt. % of hydrogen peroxide;
   (d) about 60 to about 99 wt. % of water; and
   (e) about 0.1 to about 5 wt. % of one or more acids selected from tannic acid, caffeic acid, citric acid, and gallic acid.

14. The method of claim 13, wherein the second composition comprises:
   (a) about 0.5 to about 3 wt. % of chitosan;
   (b) about 0.05 to about 2 wt. % of ascorbic acid;
   (c) about 0.01 to about 2 wt. % of hydrogen peroxide;
   (d) about 60 to about 99 wt. % of water; and
   (e) about 0.1 to about 5 wt. % of one or more acids selected from tannic acid, caffeic acid, citric acid, and gallic acid.

15. A method for treating hair comprising:
   (i) obtaining a first composition comprising chitosan;
   (ii) adding hydrogen peroxide; and
   (iii) applying the second composition to hair, wherein the second composition has a pH of about 2.5 to about 5 and comprises:
      (a) about 0.5 to about 3 wt. % of chitosan;
      (b) about 0.05 to about 2 wt. % of ascorbic acid;
      (c) about 0.01 to about 2 wt. % of hydrogen peroxide;
      (d) about 60 to about 99 wt. % of water; and
      (e) about 0.1 to about 5 wt. % of one or more acids selected from tannic acid, caffeic acid, citric acid, and gallic acid;
      wherein the weight percentages are based on a total weight of the second composition; and
   (iv) heating the hair, which has the second composition applied thereto, to a temperature of 30° C. to 200° C.

16. The method of claim 15, wherein the pH of the second composition is about 3 to about 4.

17. The method of claim 15, wherein the heating is carried out with a blow dryer, a flat iron, a heating hood, or a curling iron.

18. The method of claim 15, wherein the second composition further comprises one or more silicones.

* * * * *